(12) United States Patent
Potts et al.

(10) Patent No.: US 6,649,099 B2
(45) Date of Patent: Nov. 18, 2003

(54) METHOD OF INCORPORATING FLUID TREATMENT AGENTS INTO ABSORBENT COMPOSITES

(75) Inventors: David Charles Potts, Dunwoody, GA (US); Yen-Ling Lai, Duluth, GA (US); Ramonica Frances Green, Alpharetta, GA (US); Teri Taylor Kish, Alpharetta, GA (US); Sylvia Bandy Little, Marietta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 130 days.

(21) Appl. No.: 10/034,342

(22) Filed: Dec. 28, 2001

(65) Prior Publication Data

US 2003/0127767 A1 Jul. 10, 2003

Related U.S. Application Data

(63) Continuation-in-part of application No. 10/035,701, filed on Nov. 9, 2001, which is a continuation of application No. 09/183,170, filed on Oct. 30, 1998, now Pat. No. 6,350,711.

(51) Int. Cl.$^7$ ............................ B29B 9/04; B29B 11/02; B29B 11/14
(52) U.S. Cl. ........................................ 264/113; 264/115
(58) Field of Search ................................ 264/109–128

(56) References Cited

U.S. PATENT DOCUMENTS

| 3,338,992 A | 8/1967 | Kinney |
| 3,341,394 A | 9/1967 | Kinney |
| 3,502,538 A | 3/1970 | Petersen |
| 3,502,763 A | 3/1970 | Hartmann |
| 3,542,615 A | 11/1970 | Dobo et al. |
| 3,692,618 A | 9/1972 | Dorschner et al. |
| 3,802,817 A | 4/1974 | Matsuki et al. |
| 3,849,241 A | 11/1974 | Butin et al. |
| 4,167,464 A | 9/1979 | George |
| 4,190,563 A | 2/1980 | Bosley et al. |
| 4,340,563 A | 7/1982 | Appel et al. |
| 4,358,394 A | 11/1982 | Crews et al. |
| 4,432,833 A | 2/1984 | Breese |
| 4,462,989 A | 7/1984 | Cerami |
| 4,488,928 A | 12/1984 | Ali Khan et al. |
| 4,565,663 A | 1/1986 | Errede et al. |
| 4,614,787 A | 9/1986 | Szycher et al. |
| 4,767,586 A | 8/1988 | Radwanski et al. |

(List continued on next page.)

FOREIGN PATENT DOCUMENTS

| EP | 019 371 | 11/1980 |
| EP | 530 301 | 3/1993 |
| EP | 793 971 | 9/1997 |

(List continued on next page.)

Primary Examiner—Stephen J. Lechert, Jr.
(74) Attorney, Agent, or Firm—Pauley Petersen & Erickson (57) ABSTRACT

A method of incorporating a density modulator into an absorbent composite includes the steps of applying a density modulator solution to a pulp sheet, fiberizing the pulp sheet, and incorporating the fiberized pulp sheet into an absorbent composite. The density modulator can be applied by slot coating or by using a flooded nip. Once the density modulator is incorporated into the absorbent composite, the absorbent composite is highly wettable and, upon contact with blood-containing bodily fluids, undergoes a decrease in density, thereby increasing the absorbent capacity of the absorbent composite.

41 Claims, 6 Drawing Sheets

U.S. PATENT DOCUMENTS

| | | |
|---|---|---|
| 5,108,820 A | 4/1992 | Kaneko et al. |
| 5,108,827 A | 4/1992 | Gessner |
| 5,190,657 A | 3/1993 | Heagle et al. |
| 5,227,107 A | 7/1993 | Dickenson et al. |
| 5,281,208 A | 1/1994 | Thompson et al. |
| 5,314,582 A | 5/1994 | Nguyen et al. |
| 5,336,552 A | 8/1994 | Strack et al. |
| 5,382,400 A | 1/1995 | Pike et al. |
| 5,460,622 A | 10/1995 | Dragoo et al. |
| 5,486,167 A | 1/1996 | Dragoo et al. |
| 5,525,407 A | 6/1996 | Yang |
| 5,529,933 A | 6/1996 | Young et al. |
| 5,558,834 A | 9/1996 | Chu et al. |
| 5,700,254 A | 12/1997 | McDowall et al. |
| 5,709,852 A | 1/1998 | Gopalkrishnan et al. |
| 5,759,844 A | 6/1998 | Hiraki et al. |
| 5,762,871 A | 6/1998 | Neyer |
| 5,797,891 A | 8/1998 | Wiersma |
| 6,017,832 A | 1/2000 | Yahiaoui et al. |
| 6,043,168 A | 3/2000 | Colman et al. |
| 6,060,636 A | 5/2000 | Yahiaoui et al. |
| 6,107,268 A | 8/2000 | Yahiaoui et al. |
| 6,177,367 B1 | 1/2001 | Mathis |
| 6,231,557 B1 | 5/2001 | Krautkramer et al. |
| 6,525,125 B1 * | 2/2003 | Giardello et al. ........... 524/439 |
| 2001/0018068 A1 | 8/2001 | Lorenzi et al. |
| 2002/0040210 A1 | 4/2002 | Luccio et al. |

FOREIGN PATENT DOCUMENTS

| | | |
|---|---|---|
| WO | WO 93/21879 | 11/1993 |
| WO | 96/40300 | 12/1996 |
| WO | WO 97/24378 | 7/1997 |
| WO | WO 98/10134 | 3/1998 |
| WO | 98/17856 | 4/1998 |
| WO | 99/32706 | 7/1999 |
| WO | WO 99/61079 | 12/1999 |
| WO | WO 00/25835 | 5/2000 |
| WO | 00/26458 | 5/2000 |
| WO | WO 01/00156 | 1/2001 |
| WO | WO 01/45615 A1 | 6/2001 |
| WO | 01/47456 | 7/2001 |
| WO | 01/91684 | 12/2001 |
| WO | WO 02/45762 | 6/2002 |

* cited by examiner

METHOD OF INCORPORATING FLUID TREATMENT AGENTS INTO ABSORBENT COMPOSITES

CROSS REFERENCE TO RELATED APPLICATION

This application is a continuation-in-part of U.S. patent application Ser. No. 10/035,701 filed Nov. 9, 2001 which is a continuation of U.S. patent application Ser. No. 09/183,170 filed Oct. 30, 1998 U.S. Pat. No. 6,350,711.

BACKGROUND OF THE INVENTION

This invention relates to method of incorporating a density modifier into an absorbent composite. The resulting absorbent composite is suitable for use in personal care absorbent articles, which are particularly adapted for absorbing various blood-containing bodily fluids, such as diapers and catamenial articles including sanitary napkins and pads, tampons, wound dressings, and the like.

A wide variety of disposable absorbent articles for collecting bodily fluids are known in the art. Commercial absorbent articles include diapers, sanitary napkins, training pants, and incontinent care pads, wound dressings, tampons, and the like. Disposable products of this type include some functional elements for receiving, absorbing, and retaining fluids. Typically, such absorbent articles have an absorbent core containing cellulosic fibers, for example, wood pulp fluff, particles of highly absorbent materials, for example, superabsorbents, and an admixture of cellulosic fibers and superabsorbents. Typically, such articles include a fluid-permeable cover sheet or topsheet which typically faces the body of the user, an absorbent core, and a fluid-impermeable backsheet.

Cover sheet materials are utilized for the transport of bodily fluids into the absorbent core of personal care absorbent articles and, thus, materials used for cover sheet applications must manage distinctly different body excretions, depending upon the application and the product type. Some products must manage fluids, such as urine, while others must manage proteinaceous and viscoelastic fluids, such as menstrual discharge and fecal matter. The management of viscoelastic menstrual discharge by feminine care products such as sanitary pads and napkins is exacerbated due to the variations in composition and rheology over a broad range of elasticity. Fluid management in feminine care applications requires control of absorption of bodily fluids, control of fluid retention in the cover, control of stain size and intensity, control of rewet of fluid back to the surface, and control of the release of fluid to the absorbent core.

There are several factors which influence the flow of liquids in fibrous structures including the geometry of the pore structure in the fabrics, the nature of the solid surface (surface energy, surface charge, etc.), the geometry of the solid surface (surface roughness, grooves, etc.), the chemical/physical treatment of the solid surface, and the chemical nature of the fluid. One problem associated with absorbent articles intended for use in handling fluids comprising blood components such as feminine care products and wound dressings is the tendency of red blood cells to block the pores of the materials used for absorption of fluids in such products. Typical of such porous materials are nonwoven or fibrous web materials. The blockage of the pores of the nonwoven or fibrous web materials by the red blood cells results in a reduction in the fluid intake and the wicking capabilities of such products. In addition, in the case of feminine care products such as sanitary pads, napkins and tampons, the blockage of pores of nonwoven materials used therein by red blood cells results in increased staining. In the case of feminine care products comprising superabsorbents, the red blood cells attach themselves to the superabsorbents, resulting in blockage of the superabsorbents and a significant reduction in fluid uptake.

In the case of feminine care products such as sanitary pads and napkins, women have come to expect a high level of performance in terms of comfort and fit, retention of fluid, and minimal staining. Of utmost importance, leakage of fluid from the pad onto undergarments is regarded as totally unacceptable.

Improving the performance of feminine care products continues to be a formidable undertaking, although numerous improvements have been made in both their materials and structures. However, solutions addressing the issues arising from the presence of red blood cells in blood or menses in feminine care products, as well as other absorbent materials for handling blood-containing fluids, have not been satisfactorily implemented. It is apparent that a system which effectively handles red blood cells in a manner which addresses the issues set forth hereinabove will not only improve the distribution of incoming fluids by the absorbent material, but will also reduce the tendency toward premature failures of these absorbent articles. Furthermore, such a system that can be incorporated into a thin, discreet product that can readily absorb a large amount of such fluids would be a remarkable improvement over current absorbent systems.

Another obstacle that stands in the way of improving the performance of feminine care products is the difficulty of incorporating fluid treatment agents into absorbent composites. One method of applying fluid treatment agents to absorbent composites that has been used with success involves soaking an airlaid handsheet in the fluid treatment agent, squeezing out the excess solution, and then drying the handsheet in an oven. This approach works well for small scale production. However, it does not work for large scale production because drying the airlaid slows down the production process significantly.

There is a need or desire for a method of incorporating fluid treatment agents into absorbent composites.

SUMMARY OF THE INVENTION

In response to the discussed difficulties and problems encountered in the prior art, a new method of incorporating fluid treatment agents into absorbent composites has been discovered.

The present invention is directed to a method of incorporating a fluid treatment agent, namely a density modulator, into an absorbent composite. The method includes the steps of applying a density modulator solution to a pulp sheet. The application may be carried out by slot coating or by using a flooded nip. The pulp sheet is then fiberized. Finally, the fiberized pulp sheet is incorporated into an absorbent composite. The concentration of the density modulator solution is an important consideration. Suitably, the concentration of the density modulator solution is between about 5% and about 25%, or between about 8% and about 20%, or between about 10% and about 15% by weight of the pulp sheet.

By applying the solution to the pulp sheet in this way, the liquid is dried by the heat of the fiberizer and is uniformly distributed throughout the pulp. Also, by using more than one forming head, layers of treated material can be made. In addition, the method of this invention allows for incorporation of the density modulator into airlaid or fluff, whereas the other methods do not.

The density modulator makes the treated material in the absorbent article more wettable, thus increasing the article's intake capability, and also lowers the density of the treated material when the material comes into contact with a blood-containing fluid. By lowering the density of the treated material, the volume of the material increases, thereby providing more space in which the fluid can be contained.

The density modulator can be alkyl glycoside or any other composition that increases wettability and lowers density upon contact with blood-containing fluid. Another feature of the density modulator is that it is present in a low enough concentration that it provides wettability and affects the density of the material to which it is applied without lysing the red blood cells with which the treated material comes into contact.

In one embodiment of the invention, the absorbent composite with the density modulator incorporated therein is used to form an absorbent article, such as a catamenial device. More particularly, the absorbent composite can be used to form a liner or a containment layer, or both the liner and the containment layer.

One of the benefits of this invention derives from the fact that the red blood cells of a blood-containing fluid, having come into contact with the density modulator, are no longer able to block the flow of fluids into any superabsorbents that may be present in the absorbent material.

With the foregoing in mind, particular embodiments of the invention provide a method of making absorbent composites that are thin and discreet, can effectively handle red blood cells, and can readily absorb a large amount of blood-containing bodily fluids.

BRIEF DESCRIPTION OF THE DRAWINGS

These and other objects and features of this invention will be better understood from the following detailed description taken in conjunction with the drawings, wherein.

DESCRIPTION OF PREFERRED EMBODIMENTS

Definitions

As used herein, the term "density modulator" refers to a composition that provides greater wettability of an absorbent material and causes the density of the material to decrease upon contact with a blood-containing fluid.

As used herein, the term "nonwoven web" or "fibrous web" refers to any material comprising fibrous or fiber-like elements, usually in a random arrangement, joined by bonding points which stabilize the structure, providing at least some mechanical integrity, which form at least some small pores throughout the length and width thereof between adjacent fiber-like elements. The term also includes individual filaments and strands, yarns or tows as well as foams and films that have been fibrillated, apertured or otherwise treated to impart fabric-like properties. "Nonwoven webs" or "fibrous webs" are formed by many processes such as, for example, spunbonding, meltblowing, airlaid and bonded carded processes.

As used herein, the term "coform" or "coformed" refers to a material including a blend of natural fibers and/or synthetic polymer fibers.

As used herein, the term "spunbonding" refers to a process in which small diameter fibers are formed by extruding molten thermoplastic materials as filaments from a plurality of fine, usually circular capillaries of a spinneret with the diameter of the extruded filaments then being rapidly reduced as, for example, described in U.S. Pat. No. 4,340,563 to Appel et al., U.S. Pat. No. 3,692,618 to Dorschner et al., U.S. Pat. No. 3,802,817 to Matsuki et al., U.S. Pat. No. 3,338,992, U.S. Pat. No. 3,341,394 to Kinney, U.S. Pat. No. 3,502,763 to Hartmann, U.S. Pat. No. 3,502,538 to Levy, and U.S. Pat. No. 3,542,615 to Dobo et al. Spunbond fibers are quenched and generally not tacky when they are deposited onto a collecting surface. Spunbond fibers are generally continuous and have average diameters frequently larger than 7 microns, more particularly, between about 10 and 20 microns.

As used herein, the term "meltblowing" refers to a process in which fibers are formed by extruding a molten thermoplastic material through a plurality of fine, usually circular, die capillaries as molten threads or filaments into converging high velocity, usually heated, gas (for example air) streams which attenuate the filaments of molten thermoplastic material to reduce their diameter, which may be to microfiber diameter. Thereafter, the meltblown fibers are carried by the high velocity gas stream and are deposited on a collecting surface, often while still tacky, to form a web of randomly dispersed meltblown fibers. Such a process is disclosed, for example, by U.S. Pat. No. 3,849,241 to Butin. Meltblown fibers are microfibers which may be continuous or discontinuous and are generally smaller than 10 microns in average diameter.

As used herein, the term "bonded carded" or "bonded carded webs" refers to nonwoven webs formed by carding processes as are known to those skilled in the art and further described, for example, in U.S. Pat. No. 4,488,928 to Alikhan and Schmidt. Typically, carding processes involve starting with a blend of, for example, staple fibers with bonding fibers or other bonding components in a bulky batt that is combed or otherwise treated to provide a generally uniform basis weight. This web is heated or otherwise treated to activate the adhesive component, resulting in an integrated, usually lofty nonwoven material.

As used herein, the term "monocomponent" fiber refers to a fiber formed from one or more extruders using only one polymer. This is not meant to exclude fibers formed from one polymer to which small amounts of additives have been added for color, anti-static properties, lubrication, hydrophilicity, etc. These additives are generally present in an amount less than about 5 weight percent and more typically about 2 weight percent.

As used herein, the term "conjugate fibers" refers to fibers which have been formed from at least two polymers extruded from separate extruders but spun together to form one fiber. Conjugate fibers are also sometimes referred to as multicomponent or bicomponent fibers. The polymers are usually different from each other though conjugate fibers may be monocomponent fibers. The polymers are arranged in substantially constantly positioned distinct zones across a cross-section of the conjugate fibers and extend continuously along the length of the conjugate fibers. The configuration of such a conjugate fiber may be, for example, a sheath/core arrangement in which one polymer is surrounded by another, or may be a side-by-side arrangement, or an "islands-in-the-sea" arrangement. Conjugate fibers are taught, for example, by U.S. Pat. No. 5,108,820 to Kaneko et al., U.S. Pat. No. 5,336,552 to Strack et al., and U.S. Pat. No. 5,382,400 to Pike et al. For two component fibers, the polymers may be present in ratios of 75/25, 50/50, 25/75, or any other desired ratios.

As used herein, the term "biconstituent fibers" refers to fibers which have been formed from at least two polymers extruded from the same extruder as a blend. Biconstituent fibers do not have the various polymer components arranged in relatively constantly positioned distinct zones across the cross-sectional area of the fiber and the various polymers are usually not continuous along the entire length of the fiber, instead usually forming fibrils or protofibrils which start and end at random. Biconstituent fibers are sometimes also referred to as multiconstituent fibers. Fibers of this general type are discussed in, for example, U.S. Pat. No. 5,108,827 to Gessner.

As used herein, the term "polymer" generally includes, but is not limited to, homopolymers, copolymers, such as for example, block, graft, random and alternating copolymers, terpolymers, etc., and blends and modifications thereof. In addition, unless otherwise specifically limited, the term "polymer" includes all possible geometric configurations of the material. The configurations include, but are not limited to, isotactic, syndiotactic, and random symmetries.

As used herein, the term "absorbent material" refers to any material having fluid absorption properties.

As used herein, the term "personal care absorbent articles" refers to diapers, training pants, absorbent underpants, adult incontinence products, sanitary wipes and feminine hygiene products such as sanitary napkins, pads, and tampons.

As used herein, the term "intake" refers to the ability of an absorbent article to absorb fluid. Intake time is used to assess the quality of absorption with lower intake times denoting materials capable of rapid absorption and higher intake times denoting materials with poorer absorption.

As used herein, the term "stain" refers to fluid, wet or dry, which is present on the top surface, in, or on the bottom surface of a cover material or topsheet of a personal care absorbent article.

As used herein, the term "gradient porosity" refers to a porous system in which the average pore size in the system decreases (or increases) from one side of the system to the opposite side of the system. In the case of personal care absorbent articles employing porosity gradient nonwoven web materials in accordance with this invention, average pore sizes decrease from the side of the nonwoven web material disposed towards the topsheet or cover of the absorbent article in the direction of the liquid impervious backsheet.

"Menses simulant" is a material which simulates the viscoelastic and other properties of menses. To prepare the fluid, blood, such as defibrinated swine blood, is separated by centrifuge at 3000 rpm for 30 minutes, although other methods or speeds and times may be used if effective. The plasma is separated and stored separately, the buffy coat removed and discarded, and the packed red blood cells stored separately as well. Eggs, such as jumbo chicken eggs, are separated, the yoke and chalazae discarded, and the egg white retained. The egg white is separated into thick and thin portions by straining the white through a 1000 micron nylon mesh for about three minutes, and the thinner portion discarded. Alternative mesh sizes may be used, and the time or method may be varied provided the viscosity is at least that required. The thick portion of egg white which was retained on the mesh is collected and 80 ml is mixed with 60 ml of swine plasma. The material is then sheared by any appropriate method to achieve a homogeneous solution with a viscosity of about 7 to 15 cps at 1 $sec^{-1}$ at 22 degrees Celsius. Sixty (60) cc of swine red blood cells are added, and the contents mixed for about one minute, or until the contents appear homogeneous. The final mixture has a red blood cell content of about 30 volume percent and generally is at least within the range of 28–32 volume percent for artificial menses. The amount of egg white is about 40 weight percent.

Menstrual discharges are composed of blood, vaginal or cervical secretions and endometrial tissues, also called clots. The vaginal secretions are mainly composed of mucins. The proportions of the various components of menstrual fluid vary from woman to woman and from period to period. The proportions of these components also depend upon the age of the woman, the activity of the woman and the method of birth control used by the woman. As a result, the fluid composition can vary from 30 to 70% blood, 10 to 50% cervical secretions, and 0 to 30% endometrial tissues.

Mucin and endometrial tissues are two components that are not easily absorbed into a porous structure made of standard nonwoven materials. These two highly viscous and elastic components are often responsible for cover smearing on a pad and premature leakage (leakage without high content fluid loading in the pad).

There are several factors which influence the flow of liquids in fibrous structures including the geometry of the pore structure in the fabrics, the nature of the solid surface (surface energy, surface charge, etc.), the geometry of the solid surface (surface roughness, grooves, etc.), the chemical/physical treatment of the solid surface, the chemical nature of the fluid, and the density of the fibrous structure.

This invention, in accordance with one embodiment, provides a method of incorporating a density modulator into an absorbent composite which can be used in an absorbent article, such as a sanitary pad, napkin, tampon, wound dressing and the like, the intended purpose of which is to absorb and store blood-containing fluids. The layer or layers treated with the density modulator in the absorbent article of this invention increase in thickness and volume, providing full use of the absorbent capacity of the layers as well as improved wicking capabilities.

Figure 1:
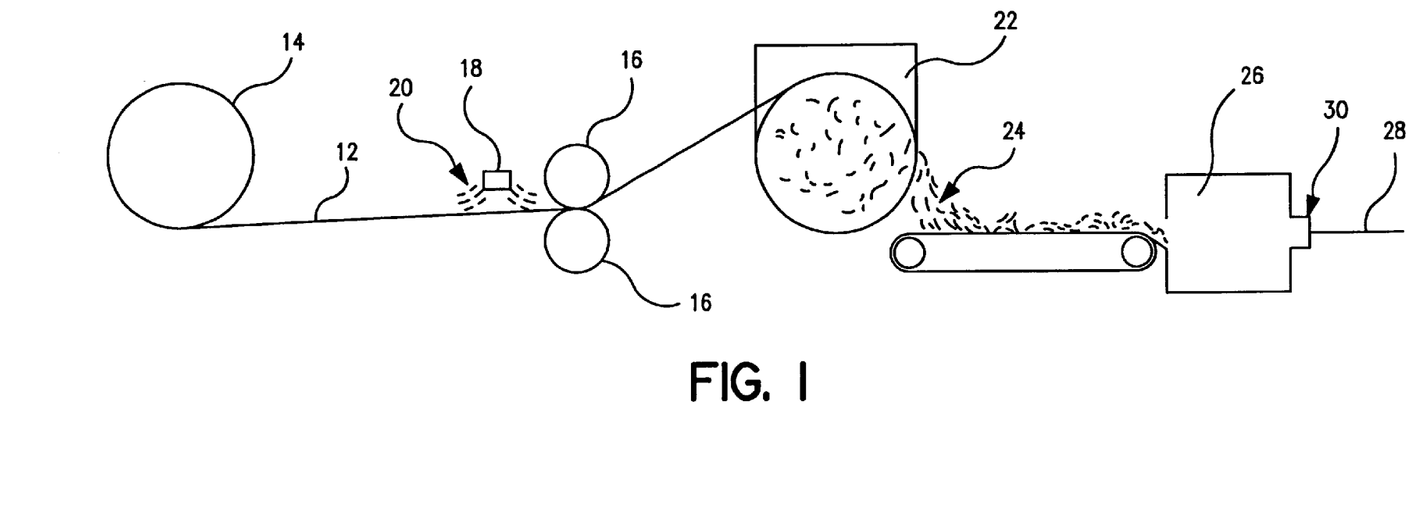
FIG. 1 is a schematic diagram of a process line that can be used to carry out the method of the invention.

Referring, for example, to FIG. 1, a process line 10 for carrying out one embodiment of the method of the invention is shown. The process line 10 includes a pulp sheet 12 that is fed from one or more supply rolls 14 to a pair of nip rolls 16. Before the pulp sheet 12 reaches the nip rolls 16, the pulp sheet 12 passes beneath a slot coating apparatus 18, known to those skilled in the art, which is essentially a bar having a slot from which the density modulator solution 20 is applied to the pulp sheet 12. After the density modulator solution 20 is applied to the pulp sheet 12, the treated pulp sheet is fed into a fiberizer 22 which individualizes the fibers within the pulp sheet 12. The fiberized pulp 24 is then fed into a forming apparatus 26 where the fiberized pulp 24 is incorporated into an absorbent composite 28. For example, the fiberized pulp 24 can be formed into a nonwoven web, such as an airlaid, coformed, airformed (formed directly into a web) or bonded carded web. Additionally, superabsorbent material can be dispersed throughout the fiberized pulp 24 for added absorbent capacity. One or more forming heads 30 can be attached to the forming apparatus 26, with a single layer of the absorbent composite 28 being produced from each of the forming heads 30.

Figure 2:
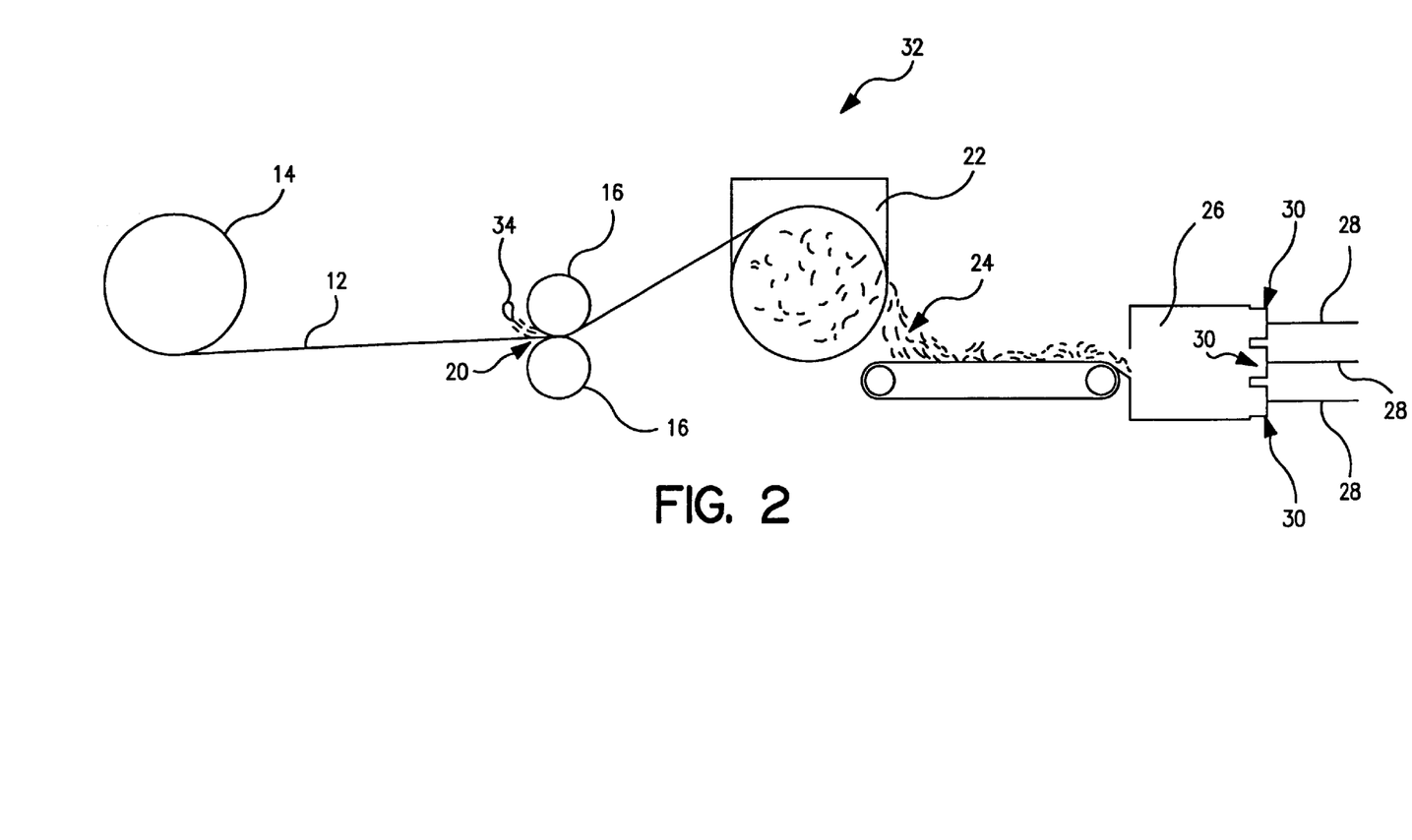
FIG. 2 is a schematic diagram of another process line that can be used to carry out the method of the invention.

FIG. 2 illustrates a process line 32 for carrying out another embodiment of the method of the invention. The process line 32 includes the pulp sheet 12 fed from one or more of the supply rolls 14 to the pair of nip rolls 16. However, instead of the slot coat apparatus, a flooded nip 34 is present and aligned adjacent the pulp sheet 12 just prior to the point where the pulp sheet 12 meets the nip rolls 16. The flooded nip 34, familiar to those skilled in the art, is an apparatus from which the density modulator solution 20 is applied to the pulp sheet 12. After the density modulator solution 20 is applied to the pulp sheet 12, the treated pulp sheet is fed into the fiberizer 22 which individualizes the fibers within the pulp sheet 12. As in the previous embodiment, the fiberized pulp 24 can then be incorporated into one or more absorbent composites 28.

Carrying out another embodiment of the method of the invention, spraying the density modulator solution 20 onto the pulp sheet 12, the liquid is dried by the heat of the fiberizer 22 and is uniformly distributed throughout the pulp. In addition, this method allows for incorporation of the density modulator into airlaid as well as fluff or airformed composite.

Suitably, the density modulator solution is applied to the pulp sheet in a concentration of between about 5% and about 30%, or between about 8% and about 20%, or between about 10% and about 15% by weight of the pulp sheet. The wet add-on value of the density modulator solution is suitably between about 3% and about 20%, or between about 4% and about 15%, or between about 5% and about 10% by weight of the pulp sheet, giving a dry add-on value of between about 0.2% and about 10%, or between about 0.5% and about 6%, or between about 0.8% and about 3% by weight of the pulp sheet. Suitably, the resulting absorbent composite has a basis weight of between about 50 and about 650 grams per square meter (gsm), or between about 100 and about 350 gsm, or between about 150 and about 275 gsm.

A wide variety of disposable personal care absorbent articles for collecting bodily fluids, which articles typically comprise nonwoven web materials, are known in the art. Disposable products of this type include some functional elements for receiving, absorbing, and retaining fluids. Typically, such absorbent articles have an absorbent core or other containment layer containing cellulosic fibers, for example, wood pulp fluff, particles of highly absorbent materials, for example, superabsorbents, and an admixture of cellulosic fibers and superabsorbents.

Figure 3:
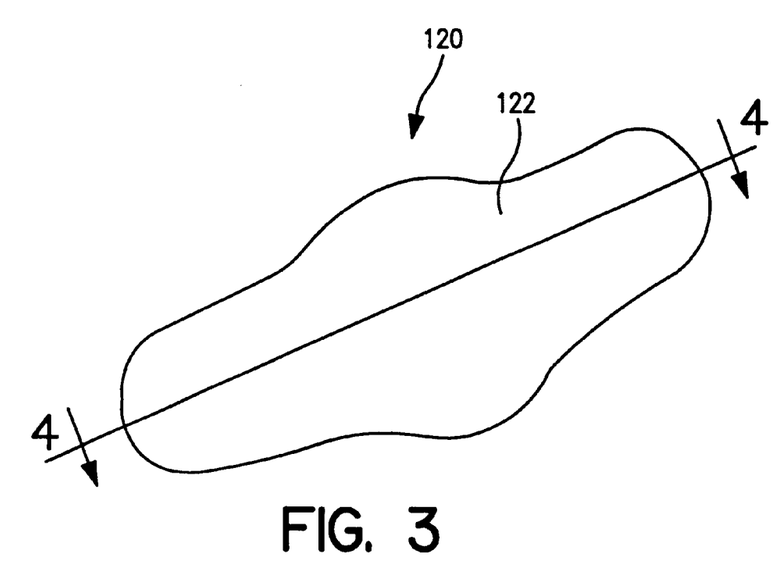
FIG. 3 is a perspective view of an absorbent article.
Figure 4:
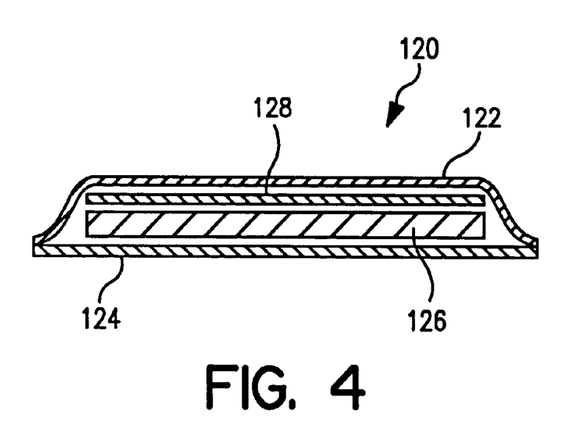
FIG. 4 is a cross-sectional view of the absorbent article of FIG. 3, taken along line 4—4.

An example of a personal care absorbent article 120 including absorbent material made in accordance with the present invention is shown in FIG. 3. A cross-section of the absorbent article 120 is shown in FIG. 4, which exhibits the various layers of the absorbent material that make up the absorbent article 120. More particularly, the absorbent article 120 may include a fluid permeable liner 122 which faces the body of the user, and on an opposite surface of the absorbent article a fluid impervious outer cover 124 that faces away from the wearer while the article is in use. Absorbent material within the article 120 may include the liner 122, as well as a containment layer 126 positioned between the liner 122 and the outer cover 124. An additional absorbent material or containment layer, namely an intake layer 128, may be positioned between the liner 122 and the containment layer 126 to provide added intake capability to the article. At least one of the layers, suitably the liner 122, the containment layer 126, or the intake layer 128, or a combination of any of these layers, is treated with the density modulator.

Liner materials are utilized for the transport of bodily fluids into the containment layer of personal care absorbent articles and, thus, materials used for liner applications must manage distinctly different body excretions, depending upon the application and the product type. Some products must manage fluids, such as urine, while others must manage proteinaceous and viscoelastic fluids, such as menstrual discharge and fecal matter. The management of viscoelastic menstrual discharge by feminine care products, or catamenial devices, such as sanitary pads and napkins, is exacerbated due to the variations in composition and rheology over a broad range of elasticity. Fluid management in feminine care applications requires control of absorption of bodily fluids, control of fluid retention in the cover, control of stain size and intensity, control of rewet of fluid back to the surface, and control of the release of fluid to the containment layer.

The absorbent material treated in accordance with this invention may be a porous, nonwoven material formed by any method known to those skilled in the art for producing nonwoven web materials. The fibers from which the nonwoven web materials may be made are produced, for example, by meltblowing or spunbonding processes, including those processes producing multicomponent, biconstituent or polymer blend fibers which are well known in the art. These processes generally use an extruder to supply melted thermoplastic polymer to a spinneret where the polymer is fiberized to yield fibers which may be staple length or longer. The fibers are then drawn, usually pneumatically, and deposited on a moving foraminous mat or belt to form the nonwoven fabric. The fibers produced in the spunbond and meltblown processes are microfibers. Alternatively, the absorbent material may be airlaid, airformed, or wetlaid. Liner material, in particular, may include a fluid permeable polymeric film.

In accordance with one embodiment of this invention, the average pore size of the pores of the nonwoven web material is in the range of about 10 microns to about 200 microns, thereby ensuring that the individual red blood cells will be able to pass through the outermost pores of the nonwoven web material into the interior thereof while also ensuring that the agglomerated red blood cells will be unable to pass through the pores to contact superabsorbents which may be present.

In accordance with one embodiment of this invention, the method may be used to form a multilayer laminate in which absorbent material layers having different average pore sizes are layered one upon another so as produce an absorbent laminate having a porosity gradient as defined hereinabove.

Alternatively, the absorbent material may be a bonded carded web. Bonded carded webs are made from staple fibers, which are usually purchased in bales. The bales are placed in a picker, which separates the fibers. Then, the fibers are sent through a combing or carding unit, which further breaks apart and aligns the staple fibers in the machine direction to form a generally machine direction-oriented fibrous nonwoven web. Once the web is formed, it is then bonded by one or more of several known bonding methods. One such bonding method is powder bonding wherein a powdered adhesive is distributed through the web and then activated, usually by heating the web and adhesive with hot air or some other heat source. Another suitable bonding method is pattern bonding wherein heated calender rolls or ultrasonic bonding equipment are used to bond the fibers together, usually in localized bond pattern, though the web can be bonded across its entire surface, if so desired. Another suitable bonding method, particularly when using bicomponent staple fibers, is through-air bonding.

As mentioned, the absorbent composite, particularly in the containment layer and/or the intake layer, may include a superabsorbent. An example of a commercially available superabsorbent polymer is FAVOR 880®, available from Stockhausen, Inc. 2401 Doyle Street Greensboro, N.C. 27406.

A suitable density modulator for use in the method of this invention can be alkyl glycoside. An example of a commercially available alkyl glycoside is GLUCOPON 220, an octylpolyglycoside available from Cognis Corporation, 3304 Westinghouse Boulevard, P.O. Box 411729, Charlotte, N.C. Alkyl glycosides, such as GLUCOPON 220, are commonly used as surfactants and are known to lyse red blood cells. However, in the present invention, the alkyl glycoside or other density modulator is applied to the absorbent article in such a low concentration that the red blood cells that come into contact with the treated layer(s) of the absorbent article are not lysed. Instead, the density modulator has the effect of reducing the density of the treated layer(s). More particularly, the decrease in density is apparent by the increase in thickness of the layer. Typically, the thickness of the layer increases by at least about 12%, or by at least about 20%, or by at least about 30%. The increase in thickness caused by the density modulator is demonstrated in the Example below.

The density reduction and increased thickness are indications of an increased volume of the treated layer(s). Without wishing to be bound by theory, it is believed that the hydroxyl groups of the density modulator interfere with the cellulose fibers within the absorbent layers of the absorbent article and prevent the fibers from bonding to one another. The lack of bonding provides greater capacity within the layers for absorbing and containing fluids. Additionally, the lack of bonding also provides for better wicking capability since viscoelastic fluids flow better through a material with larger pores.

EXAMPLE

Figure 5:
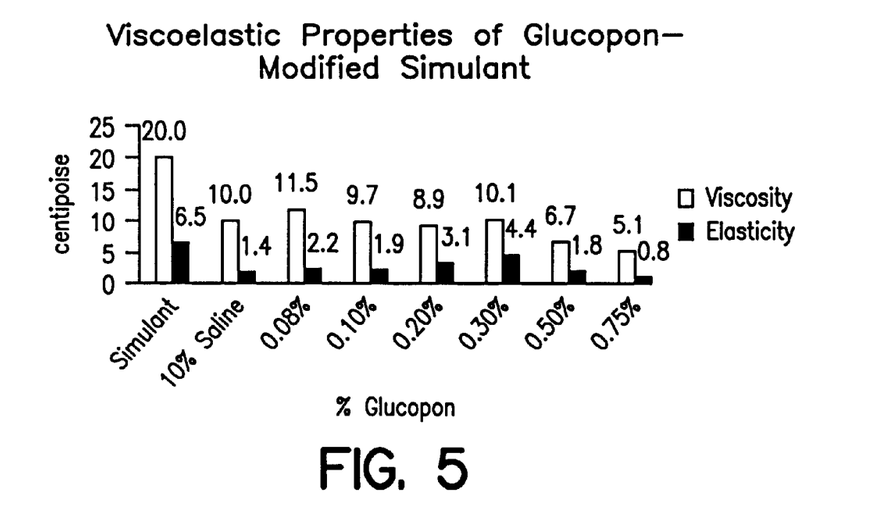
FIG. 5 is a graphical representation of the viscoelastic properties of GLUCOPON-modified simulant as demonstrated in the Example herein.

Bench testing was conducted to investigate the effect of GLUCOPON 220 on the physical properties of menses simulant. First, a 90% southern softwood pulp fluff/10% KoSa T-255 binder, 250 grams per square meter (gsm), 0.14 grams per cubic centimeter (g/cc) airlaid web was treated with various concentrations of GLUCOPON 220 and was then tested for changes in viscoelastic properties upon exposure to menses simulant, compared to an untreated control layer of the airlaid material. The was carried out using a Vilastics III rheometer, available from Vilastic Scientific, located in Austin, Tex., operating at a frequency of 0.1 Hz. The results are shown in Table 1, with a graphical representation of the data shown in FIG. 5.

TABLE 1

Viscoelastic Properties of GLUCOPON-Modified Menses Simulant

| Sample | Add-On | Viscosity | Elasticity |
|---|---|---|---|
| 1 (control) | none | 20.0 | 6.5 |
| 2 | 10% Silane | 10.0 | 1.4 |
| 3 | 0.08% GLUCOPON | 11.5 | 2.2 |
| 4 | 0.10% GLUCOPON | 9.7 | 1.9 |
| 5 | 0.20% GLUCOPON | 8.9 | 3.1 |
| 6 | 0.30% GLUCOPON | 10.1 | 4.4 |
| 7 | 0.50% GLUCOPON | 6.7 | 1.8 |
| 8 | 0.75% GLUCOPON | 5.1 | 0.8 |

The addition of GLUCOPON solution at the 0.8% and 3% levels does not yield a significant decrease in the viscoelastic properties of menses simulant over saline. Therefore, it is a high probability that GLUCOPON is not effectively lysing red blood cells at these levels.

Figure 6:
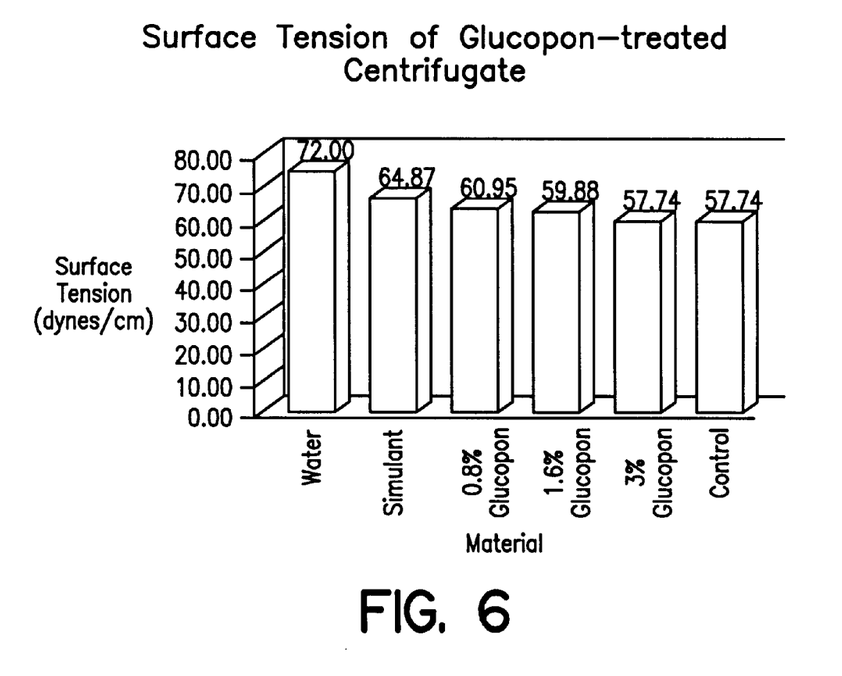
FIG. 6 is a graphical representation of the effect of GLUCOPON on the surface tension of menses simulant as demonstrated in the Example herein.

Next, the 90% southern softwood pulp fluff/10% KoSa T-255 binder, 250 gsm, 0.14 g/cc airlaid web was again treated with various concentrations of GLUCOPON 220 and was then tested for changes in surface tension of menses simulant upon exposure to the treated material, compared to an untreated control layer of the airlaid material. The surface tension of the various mixtures was determined using a Fisher Surface Tensiomat Model 21 and the duNouy Ring Method. The results are shown in Table 2, with a graphical representation of the data shown in FIG. 6.

TABLE 2

Viscoelastic Properties of GLUCOPON-Modified Menses Simulant

| Sample | Add-On | Surface Tension (dynes/cm) |
|---|---|---|
| 1 | Water | 72.00 |
| 2 | Simulant | 64.87 |
| 3 | 0.08% GLUCOPON | 60.95 |
| 4 | 1.6% GLUCOPON | 59.88 |
| 5 | 3% GLUCOPON | 57.74 |
| 6 (control) | None | 57.74 |

GLUCOPON-treated materials did not decrease the surface tension of menses simulant centrifugate over the control material.

Figure 7:
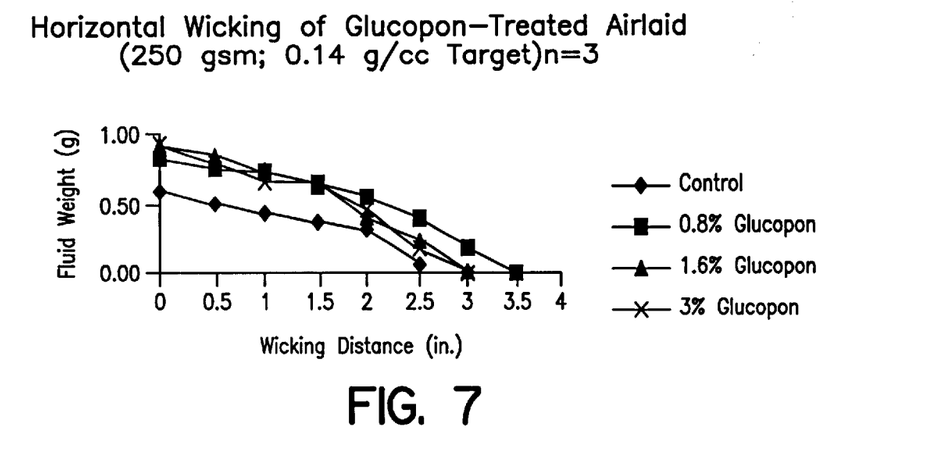
FIG. 7 is a graphical representation of horizontal wicking of GLUCOPON-treated airlaid as demonstrated in the Example herein.
Figure 8:
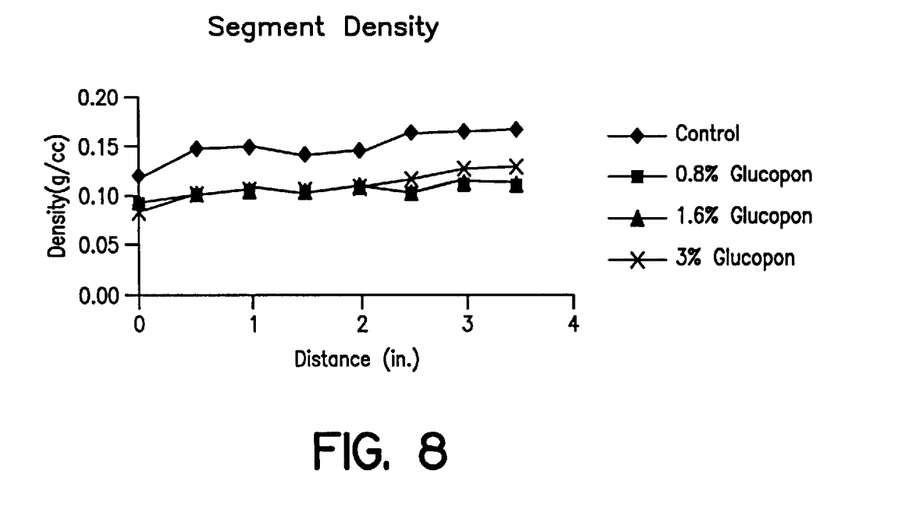
FIG. 8 is a graphical representation of density changes per material segment during the horizontal wicking testing shown in FIG. 7.

Next, the 90% southern softwood pulp fluff/10% KoSa T-255 binder, 250 gsm, 0.14 g/cc airlaid web was treated with various concentrations of GLUCOPON 220 and was then tested for horizontal wicking and density upon exposure to menses simulant, compared to an untreated control layer of the airlaid material. Wicking results were determined by a method described in U.S. Pat. No. 5,314,582 issued to Nguyen et al. Wicking was performed in a horizontal mode, at ambient conditions, with no weight used to confine samples. One-inch by eight-inch samples (eight inches in machine direction) were used, with a sample size of five. Results are reported as the distance wicked (inches) in twenty minutes. The results are shown in Table 3, with a graphical representation of the data shown in FIGS. 7 and 8.

TABLE 3

Horizontal Wicking Results of GLUCOPON-Treated Airlaid

| Wicking Distance (inches) | Control | | 0.8% GLUCOPON | | 1.6% GLUCOPON | | 3% GLUCOPON | |
|---|---|---|---|---|---|---|---|---|
| | Fluid Weight (g) | Density (g/cc) | Fluid Weight (g) | Density (g/cc) | Fluid Weight (g) | Density (g/cc) | Fluid Weight (g) | Density (g/cc) |
| 0   | 0.6  | 0.12  | 0.8  | 0.09 | 0.9  | 0.09 | 0.9  | 0.08 |
| 0.5 | 0.5  | 0.14  | 0.75 | 0.10 | 0.8  | 0.10 | 0.75 | 0.10 |
| 1   | 0.45 | 0.14  | 0.75 | 0.11 | 0.75 | 0.11 | 0.7  | 0.11 |
| 1.5 | 0.35 | 0.135 | 0.7  | 0.10 | 0.7  | 0.10 | 0.7  | 0.10 |
| 2   | 0.3  | 0.14  | 0.6  | 0.11 | 0.4  | 0.11 | 0.45 | 0.11 |
| 2.5 | 0.1  | 0.16  | 0.4  | 0.10 | 0.25 | 0.10 | 0.2  | 0.12 |
| 3   | —    | 0.16  | 0.2  | 0.12 | 0    | 0.12 | 0    | 0.13 |
| 3.5 | —    | 0.17  | 0    | 0.12 | —    | 0.12 | —    | 0.13 |

Figure 9:
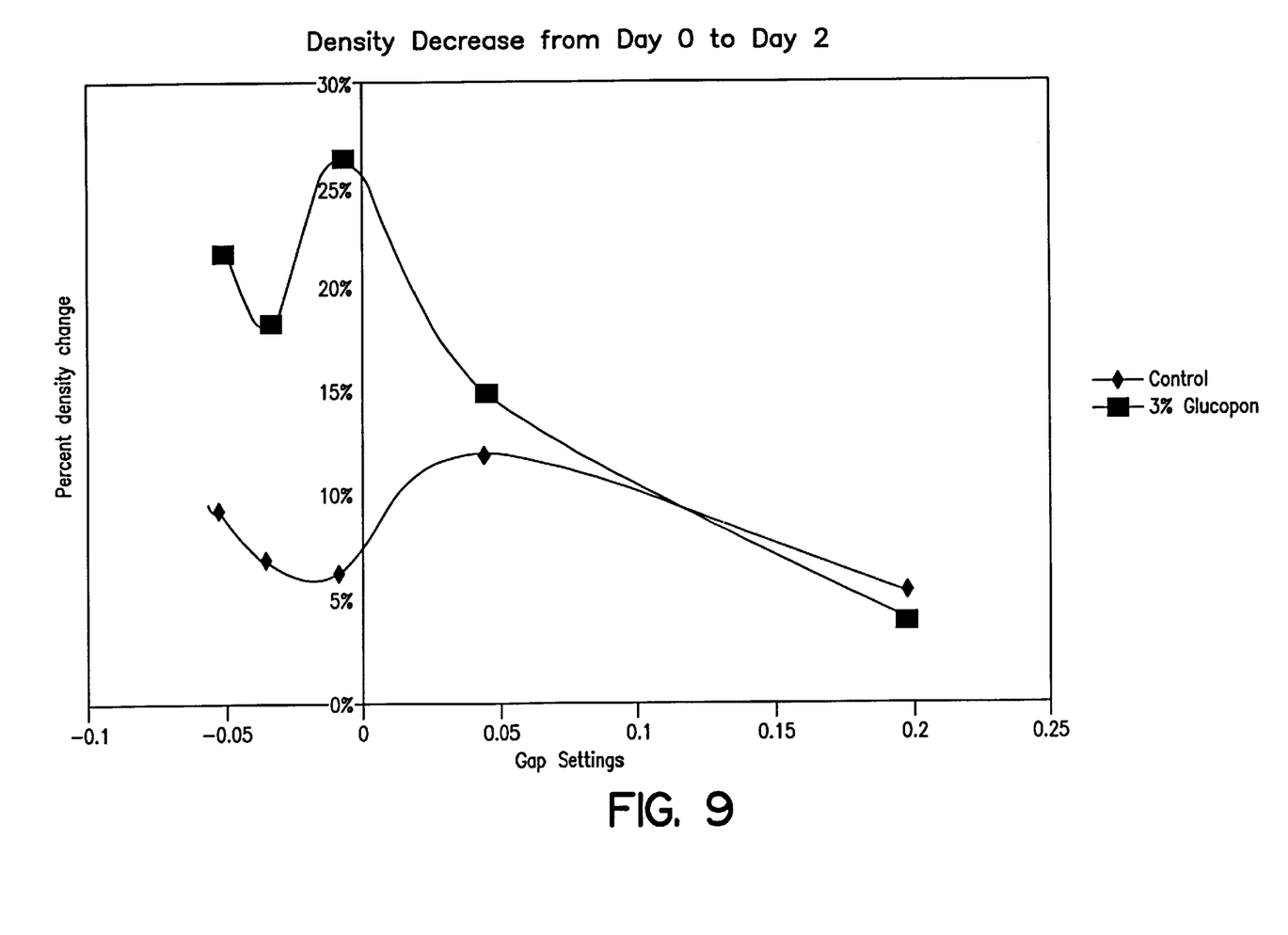
FIG. 9 is a graphical representation of density changes over a 2-day period as a function of gap settings, or distance between calender rolls, for an airlaid material and a GLUCOPON-treated airlaid material.

GLUCOPON-treated materials did provide better X-Y fluid distribution in horizontal wicking tests. This same testing also showed that although all materials were made to a target density of 0.14 g/cc, materials treated with GLUCOPON were less dense than the control at the time of testing. In addition, FIG. 9 shows the changes in density over a 2-day period as a function of the gap setting or distance between calender rolls through which the material passes as it is made, for both airlaid material alone and 3% GLUCOPON-treated airlaid material. As can be seen in FIG. 9, the GLUCOPON-treated material had a significantly greater density change compared to the control material, particularly in the highly compressed airlaid materials which passed through tightly set calender rolls. All of these results suggest that GLUCOPON acts as a wettable debonder when added to airlaid material.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

We claim:

1. A method of incorporating a density modulator into an absorbent composite, comprising the steps of:
   applying a density modulator solution to a pulp sheet;
   fiberizing the pulp sheet; and
   incorporating the fiberized pulp into an absorbent composite.

2. The method of claim 1, comprising the step of spraying the density modulator solution onto the pulp sheet.

3. The method of claim 1, comprising the step of applying the density modulator solution to the pulp sheet by slot coating the density modulator onto the pulp sheet.

4. The method of claim 1, comprising the step of using a flooded nip to apply the density modulator solution to the pulp sheet.

5. The method of claim 1, comprising the step of using multiple forming heads to form multiple layers of the absorbent composite.

6. The method of claim 1, wherein the density modulator solution is applied to the pulp sheet at a solution concentration of between about 5% and about 30% by weight of the pulp sheet.

7. The method of claim 1, wherein the density modulator solution is applied to the pulp sheet at a solution concentration of between about 8% and about 20% by weight of the pulp sheet.

8. The method of claim 1, wherein the density modulator solution is applied to the pulp sheet at a solution concentration of between about 10% and about 15% by weight of the pulp sheet.

9. The method of claim 1, wherein the density modulator solution is applied to the pulp sheet at a wet add-on value of between about 3% and about 20% by weight of the pulp sheet.

10. The method of claim 1, wherein the density modulator solution is applied to the pulp sheet at a wet add-on value of between about 4% and about 15% by weight of the pulp sheet.

11. The method of claim 1, wherein the density modulator solution is applied to the pulp sheet at a wet add-on value of between about 5% and about 10% by weight of the pulp sheet.

12. The method of claim 1, wherein the density modulator solution is applied to the pulp sheet at a dry add-on value of between about 0.2% and about 7% by weight of the pulp sheet.

13. The method of claim 1, wherein the density modulator solution is applied to the pulp sheet at a dry add-on value of between about 0.5% and about 5% by weight of the pulp sheet.

14. The method of claim 1, wherein the density modulator solution is applied to the pulp sheet at a dry add-on value of between about 0.8% and about 3% by weight of the pulp sheet.

15. The method of claim 1, wherein the density modulator comprises alkyl glycoside.

16. The method of claim 1, wherein the absorbent composite comprises a nonwoven web material selected from the group consisting of spunbond, meltblown, airlaid, airformed, coformed, and bonded carded.

17. The method of claim 16, wherein the absorbent composite comprises at least one superabsorbent dispersed throughout the nonwoven web material.

18. The method of claim 1, wherein the absorbent composite with the pulp layer incorporated therein has a basis weight in a range of between about 50 and about 650 grams per square meter.

19. The method of claim 1, wherein the absorbent composite with the pulp layer incorporated therein has a basis weight in a range of between about 100 and about 350 grams per square meter.

20. The method of claim 1, wherein the absorbent composite with the pulp layer incorporated therein has a basis weight in a range of between about 150 and about 275 grams per square meter.

21. A method of incorporating alkyl glycoside into an absorbent composite, comprising the steps of:
   slot coating an alkyl glycoside solution onto a pulp sheet;
   fiberizing the pulp sheet; and
   incorporating the fiberized pulp into an absorbent composite.

22. The method of claim 21, comprising the step of using multiple forming heads to form multiple layers of the absorbent composite.

23. The method of claim 21, wherein the alkyl glycoside solution is applied to the pulp sheet at a solution concentration of between about 5% and about 30% by weight of the pulp sheet.

24. The method of claim 21, wherein the alkyl glycoside solution is applied to the pulp sheet at a solution concentration of between about 8% and about 20% by weight of the pulp sheet.

25. The method of claim 21, wherein the alkyl glycoside solution is applied to the pulp sheet at a solution concentration of between about 10% and about 15% by weight of the pulp sheet.

26. The method of claim 21, wherein the absorbent composite comprises a nonwoven web material selected from the group consisting of spunbond, meltblown, airlaid, airformed, coformed, and bonded carded.

27. The method of claim 26, wherein the absorbent composite comprises at least one superabsorbent dispersed throughout the nonwoven web material.

28. A method of incorporating alkyl glycoside into an absorbent composite, comprising the steps of:
   using a flooded nip to apply an alkyl glycoside solution onto a pulp sheet;
   fiberizing the pulp sheet; and
   incorporating the fiberized pulp into an absorbent composite.

29. The method of claim 28, comprising the step of using multiple forming heads to form multiple layers of the absorbent composite.

30. The method of claim 28, wherein the alkyl glycoside solution is applied to the pulp sheet at a solution concentration of between about 5% and about 30% by weight of the pulp sheet.

31. The method of claim 28, wherein the alkyl glycoside solution is applied to the pulp sheet at a solution concentration of between about 8% and about 20% by weight of the pulp sheet.

32. The method of claim 28, wherein the alkyl glycoside solution is applied to the pulp sheet at a solution concentration of between about 10% and about 15% by weight of the pulp sheet.

33. The method of claim 28, wherein the absorbent composite comprises a nonwoven web material selected from the group consisting of spunbond, meltblown, airlaid, airformed, coformed, and bonded carded.

34. The method of claim 33, wherein the absorbent composite comprises at least one superabsorbent dispersed throughout the nonwoven web material.

35. A method of incorporating alkyl glycoside into an absorbent composite, comprising the steps of:
   spraying an alkyl glycoside solution onto a pulp sheet;
   fiberizing the pulp sheet; and
   incorporating the fiberized pulp into an absorbent composite.

36. The method of claim 35, comprising the step of using multiple forming heads to form multiple layers of the absorbent composite.

37. The method of claim 35, wherein the alkyl glycoside solution is applied to the pulp sheet at a solution concentration of between about 5% and about 30% by weight of the pulp sheet.

38. The method of claim 35, wherein the alkyl glycoside solution is applied to the pulp sheet at a solution concentration of between about 8% and about 20% by weight of the pulp sheet.

39. The method of claim 35, wherein the alkyl glycoside solution is applied to the pulp sheet at a solution concentration of between about 10% and about 15% by weight of the pulp sheet.

40. The method of claim 35, wherein the absorbent composite comprises a nonwoven web material selected from the group consisting of spunbond, meltblown, airlaid, airformed, coformed, and bonded carded.

41. The method of claim 40, wherein the absorbent composite comprises at least one superabsorbent dispersed throughout the nonwoven web material.

* * * * *